United States Patent [19]

Angelucci et al.

[11] Patent Number: 4,563,444
[45] Date of Patent: Jan. 7, 1986

[54] ANTHRACYCLINE GLYCOSIDES, USE AND COMPOSITIONS CONTAINING SAME

[75] Inventors: Francesco Angelucci; Sergio Penco, both of Milan; Federico Arcamone, Nerviano, all of Italy

[73] Assignee: Farmitalia Carlo Erba S.p.A., Italy

[21] Appl. No.: 621,681

[22] Filed: Jun. 18, 1984

Related U.S. Application Data

[63] Continuation of Ser. No. 382,144, May 26, 1982, Pat. No. 4,465,671.

[51] Int. Cl.$^4$ .................. A61K 31/71; C07H 15/24
[52] U.S. Cl. .................................. 514/34; 536/64
[58] Field of Search .............. 536/6.4; 424/180; 514/34

[56] References Cited

U.S. PATENT DOCUMENTS

| | | | |
|---|---|---|---|
| 4,046,878 | 9/1977 | Patelli et al. | 536/6.4 |
| 4,199,571 | 4/1980 | Penco et al. | 536/6.4 |
| 4,247,545 | 1/1981 | Cassinelli et al. | 536/6.4 |
| 4,355,026 | 10/1982 | Umezawa et al. | 536/6.4 |

FOREIGN PATENT DOCUMENTS 0044954  2/1982  European Pat. Off. ............ 536/6.4

Primary Examiner—Jonnie R. Brown
Assistant Examiner—Elli Peselev
Attorney, Agent, or Firm—Sheldon Palmer

[57]  ABSTRACT

Anthracycline glycosides of the formula (I)

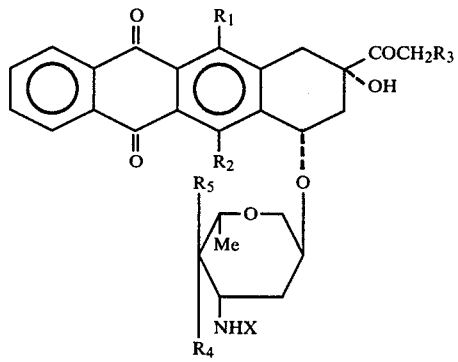

wherein one of $R_1$ and $R_2$ is hydrogen and the other of $R_1$ and $R_2$ is hydroxy, each of $R_3$, $R_4$ and $R_5$ is independently selected from the group consisting of hydrogen and hydroxy and X is hydrogen or trifluoroacetyl, with the provisos that $R_4$ and $R_5$ are not simultaneously hydroxy and that if $R_3$ is hydroxy, then X is hydrogen, which are useful in treating certain mammalian tumors are prepared by condensing an aglycone of the formula (II)

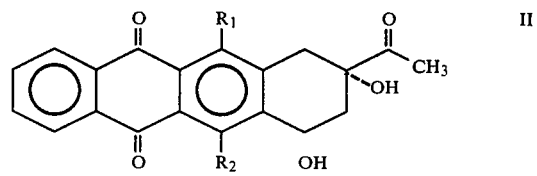

wherein $R_1$ and $R_2$ are defined as above, with a suitable protected halosugar, after which the protecting groups are removed.

7 Claims, No Drawings

ANTHRACYCLINE GLYCOSIDES, USE AND COMPOSITIONS CONTAINING SAME

This is a continuation of application Ser. No. 382,144 filed May 26, 1982, now U.S. Pat. No. 4,465,671, issued 8-14-84.

BACKGROUND OF THE INVENTION

1. Field of the Invention

The present invention relates to a new class of anthracycline glycosides having antitumor activity, methods for their preparation, pharmaceutical compositions containing them and the use thereof in treating certain mammalian tumors. The invention also relates to the aglycones of the novel glycosides and certain novel intermediates.

2. Prior Art

The new anthracyclines of the invention are related to the known antitumor glycosides daunorubicin and doxorubicin, both of which are amply described in the literature and both of which are at present being clinically used in treating certain tumors.

SUMMARY OF THE INVENTION

The invention provides, in one aspect thereof, a new class of anthracycline glycosides of the formula (I):

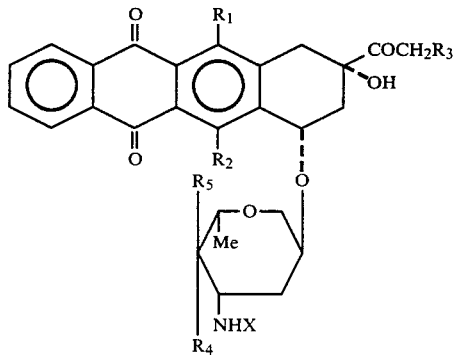

wherein one of $R_1$ and $R_2$ is hydrogen and the other of $R_1$ and $R_2$ is hydroxy, each of $R_3$, $R_4$ and $R_5$ is independently selected from the group consisting of hydrogen and hydroxy and X is hydrogen or trifluoroacetyl, with the provisos that $R_4$ and $R_5$ are not simultaneously hydroxy and that if $R_3$ is hydroxy, then X is hydrogen.

The new anthracycline glycoside antibiotics of the invention, i.e., those of formula (I), are condensation products of (a) a novel tetracyclic aglycone, i.e., anthracyclinones having a hydroxy-anthraquinone chromophoric system of the formula II

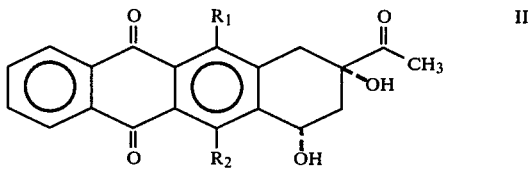

wherein $R_1$ and $R_2$ are as defined above and (b) a protected halosugar of the formula III

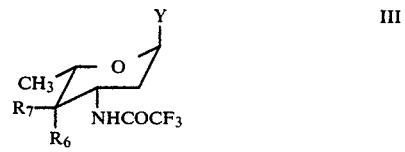

wherein Y is a halogen, preferably chlorine, and each of $R_6$ and $R_7$ is independently selected from the group consisting of hydrogen and trifluoroacetoxy, with the proviso that $R_6$ and $R_7$ are not simultaneously trifluoroacetoxy.

Accordingly, in another aspect thereof the invention provides the new class of aglycones of the formula (II).

The reaction scheme for the preparation of the anthracyclinones (II) is set forth below:

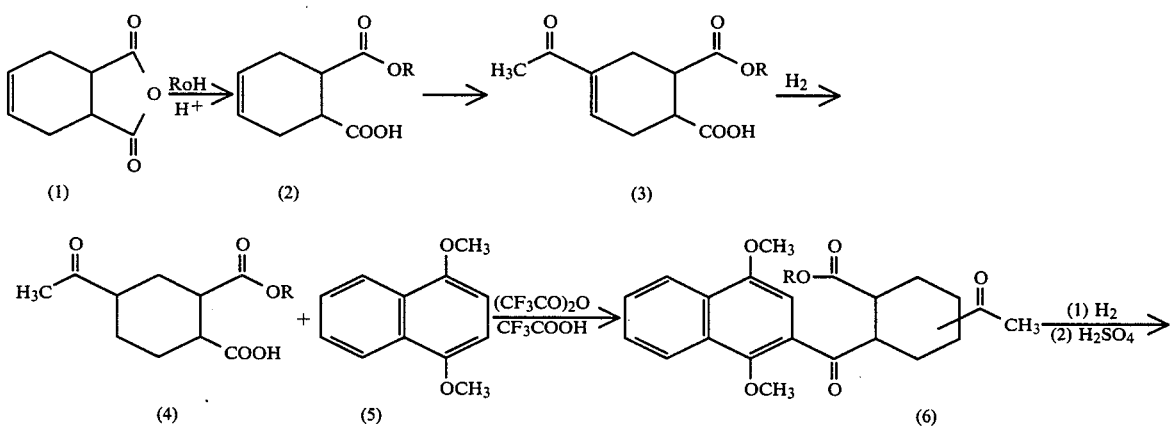

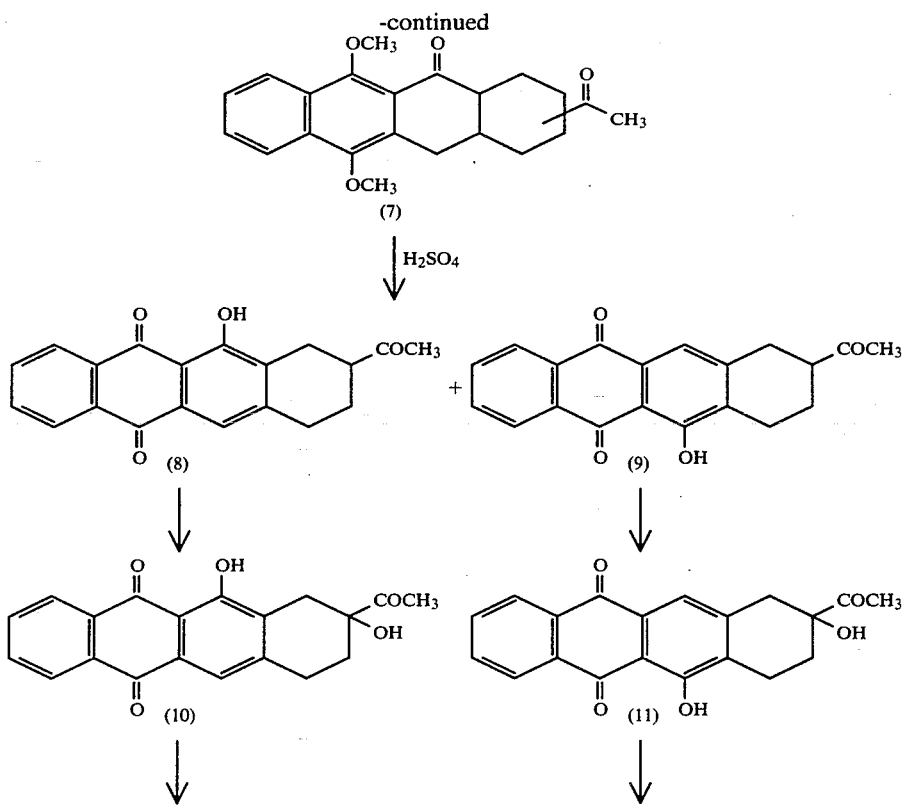

The actual starting materials for the reaction sequences are 1,2,3,6-tetrahydrophthalic anhydride (1) and 1,4-dimethoxynaphthalene (5). Compound (1) is treated with an alcohol of the formula ROH, wherein R is alkyl, substituted alkyl or aryl group, to yield the corresponding monoester (2), which is then subjected to a Friedel-Crafts reaction with acetyl chloride followed by mild alkaline treatment to give the corresponding α,β-unsaturated ketone (3). The acylation reaction is a regiospecific process giving only the C-4 acetyl derivative. The catalytic reduction of (3) quantitatively affords the acid (4) which is a key intermediate in the synthesis of the tetracyclic chromophore. The acid (4) is promptly converted to (6) (mixture of two isomers) by reaction with 1,4-dimethoxy-naphthalene (5) in the presence of trifluoroacetic anhydride and trifluoroacetic acid. The catalytic reduction of the benzylic carbonyl function of (6), followed by treatment with sulphuric acid at room temperature affords the mixture of tetracyclic isomers (7). Treatment of (7) with sulphuric acid at 80° C. gives a mixture of the new athracyclinones (8) and (9). The introduction of hydroxyl groups to give (10) and (11) is carried out by conventional methods, which have already been described. In fact the procedures followed for the oxidation of the ketones (8) and (9) to the corresponding hydroxyketones (10) and (11) are those employed with representative 20-ketosteroids [i; KOt.Bu/$O_2$, DMF, −20° C.; ii; (EtO)$_3$P, DMF, −20° C.; J. N. Garden et al, J. Org. Chem., 33, 3294, (1968)]; or i; [Ac$_2$O, HClO$_4$; ii; m-chloroperbenzoic acid; J. Attenburrow et al, J. Chem. Soc., 4547, (1961)].

Finally, the introduction of the 7-hydroxyl groups in compounds (10) and (11) is accomplished by benzylic bromination followed by solvolysis [C. M. Wong et al, Can. J. Chem., 51, 446 (1973)]. The optical resolution is carried out by the conventional method of conversion to diastereoisomeric derivatives using a chiral resolving agent (C. T. Eliel, "Stereochemistry of Carbon Compounds", McGraw Hill, 1962 Chapter 4) and affords (+) 4-demethoxy-6-deoxydaunomycinone (II; $R_1$=OH, $R_2$=H) and (+) 4-demethoxy-11-deoxydaunomycinone (II; $R_1$=H, $R_2$=OH).

The racemic anthracyclinones II may be condensed with the protected halo-sugars 1-chloro-N,O-ditrifluoroacetyldaunosamine (III; Y=Cl, $R_6$=CF$_3$COO, $R_7$=H), 1-chloro-N,O-ditrifluoroacetyl-4-epi-daunosamine (III; Y=Cl, $R_6$=H, $R_7$=CF$_3$COO) and 1-chloro-N-trifluoroacetyl-4-deoxy-daunosamine (III; Y=Cl, $R_6$=$R_7$=H) in the presence of silver trifluoromethanesulphonate to give an easily separated mixture of protected anthracycline α-glycosides 7S:9S and 7R:9R, following the method described in U.S. Pat. No. 4,107,423 owned by the assignee hereof.

Removal of the O-trifluoroacetyl group, if present, by treatment with methanol leads to the anthracycline glycosides I (X=COCF$_3$, $R_3$=H). Mild alkaline hydrolysis removes the N-trifluoroacetyl group to give the daunorubicin derivatives I (X=$R_3$=H), which may be converted to the corresponding doxorubicin derivatives I(X=H, $R_3$=OH) by 14-bromination and treatment with sodium formate in accordance with the method described in U.S. Pat. No. 3,803,124, owned by the unrecorded assignee hereof.

The processes described hereinabove are within the scope of the invention, and accordingly, in another aspect thereof the invention provides such processes.

As is apparent from the foregoing, these processes involve the preparation and use of several novel intermediates. These too are within the scope of the present invention.

In yet another aspect thereof, the invention provides pharmaceutical compositions comprising an anthracycline glycoside according to the invention in admixture with a pharmaceutically acceptable diluent or carrier therefor.

Finally, the invention provides methods of treating certain mammalian tumors using the new anthracycline glycosides of the invention.

DETAILED DESCRIPTION OF THE INVENTION

The invention will now be described in greater detail in the following preparative examples.

EXAMPLE I

Preparation of monomethyl 1,2,3,6-tetrahydrophthalate [(2)R=CH$_3$]

A solution of 50 g (0.329 mol of 1,2,3,6-tetrahydrophthalic anhydride (1) in a mixture of 200 ml of methylene dichloride and 300 ml of methanol containing 1 g of p toluenesulphonic acid was refluxed for 4 hours. The solvents were then evaporated off under reduced pressure, and the residue was dissolved in chloroform, washed with water and evaporated to dryness to give 56 g of the title compound (yield 83%), which was recrystallized from petroleum ether (60°); m.p. 85° C. TLC on kieselgel plates Merck F$_{254}$ (chloroform:acetone, 2:1 by volume): Rf 0.28

EXAMPLE II

Preparation of monomethyl 4-acetyl-1,2,3,6-tetrahydrophthalate [(3)R=CH$_3$]

To a suspension of 85 g (0.64 mol) of anhydrous aluminum trichloride in 1.5 liters of anhydrous methylene dichloride under stirring, in a nitrogen atmosphere 75 ml (1 mol) of acetyl chloride were added dropwise at −5° C. Consecutively, 40 g (0.217 mol) of the compound prepared in Example I in 750 ml of anhydrous methylene dichloride were added over a period of 2 hours. The reaction mixture was kept at −5° C. for 6 hours and then at room temperature overnight. After the addition of 1 kg of ice, the organic phase was separated off, washed with water, and evaporated to a residue. The residue, dissolved in 500 ml of methanol, was treated with 50 g of potassium carbonate at room temperature for 5 hours. After filtration, the solvent was evaporated off and the residue was dissolved in water and washed with chloroform. The aqueous alkaline solution was adjusted to pH 3 and extracted repeatedly with chloroform. The residue obtained by evaporating off the solvent was purified by chromatography on a column of silicic acid using the solvent system chloroform:acetone (95:5 by volume). 28 g (57% overall yield) of the title compound were obtained and recrystallized from diethyl ether:petroleum ether, m.p. 94°–96° C. TLC on kieselgel plates Merck F$_{254}$ (chloroform:acetone 2:1 by volume): Rf 0.22

IR (KBr): 1660 cm$^{-1}$ C=O of α,β-unsaturated ketone, 1690 cm$^{-1}$ C=O of acid, 1720 cm$^{-1}$ C=O of ester.

PMR (CDCl$_3$): 2.33 S δ (s, 3H, CO$\underline{\text{CH}}_3$), 2.55–2.95 (m, 4H, $\underline{\text{CH}}_2$—C′=CH—$\underline{\text{CH}}_2$), 3.00–3.30 (m, 2H, CH$_3$OCO$\underline{\text{CH}}$, HOCO$\underline{\text{CH}}$), 3.70 (s, 3H, COO$\underline{\text{CH}}_3$), 6.91 (m, 1H, $\underline{\text{CH}}$=), 9.81 (s, 1H, COO$\underline{\text{H}}$).

EI-MS: m/e 226 (M+), m/e 208 (M+—H$_2$O), m/e 195 (M+—OCH$_3$), m/e 180 (M+—H$_2$O—CO), m/e 121 (M+—H$_2$O—CO—COOCH$_3$).

EXAMPLE III

Preparation of monomethyl 4-acetyl-perhydrophthalate [(4) R=CH$_3$]

A solution of 4.6 g of the compound prepared in Example II in 120 ml of ethanol was hydrogenated at room temperature and 1 atm. in the presence of 0.6 g of 10% palladium-on-charcoal as catalyst. Evaporation of the solvent afforded the title compound in quantitative yield.

IR spectrum (film): 1680 cm$^{-1}$ CO of acid, 1710 cm$^{-1}$ CO of ketone, 1730 cm$^{-1}$ CO of ester.

PMR (CDCl$_3$): 1.5–2.6 δ (m, 8H), 2.18 (s, 3H, CO$\underline{\text{CH}}_3$), 3.28 (m, 1H), 3.70 (s, 3H, O$\underline{\text{CH}}_3$), 8.53 (bs, 1H, COO$\underline{\text{H}}$),

EXAMPLE IV

Preparation of 1,4-diemthoxy-3-(2′-methoxycarbonyl-4′-acetyl-cyclohexlcarbonyl)-naphthalene and 1,4-dimethoxy-3-(2′-methoxycarbonyl-5′-acetyl-cyclohexylcarbonyl)naphthalene [(6) R=CH$_3$]

A solution of 3.2 g; 0.017 mol of 1,4-dimethoxynaphthalene and 4.0 g; 0.017 mol of the compound prepared in Example III in 50 ml of trifluoroacetic anhydride and 25 ml of trifluoroacetic acid was refluxed for 24 hours. The residue, obtained by evaporting off the solvents under reduced pressure, was dissolved in chloroform and washed with an aqueous saturated solution of sodium bicarbonate and then with water. The residue, obtained by evaporation of the solvent, was purified on a column of silica gel, using chloroform as the eluting solvent, to give 3.5 g of a mixture of the isomeric title compounds.

TLC kieselgel plates Merck F$_{254}$ (chloroform:acetone 98:2 by volume). Rf 0.3

FD-MS: m/e 398 (M+).

IR (film): 1660 cm$^{-1}$ CO of α,β-unsaturated ketone, 1710 cm$^{-1}$ CO of ketone, 1720 cm$^{-1}$ CO of ester.

PMR (CDCl$_3$): 1.5–2.3 δ (m, 8H), 2.18 (s, 3H, CO$\underline{\text{CH}}_3$), 3.67 (s, 3H, COO$\underline{\text{CH}}_3$), 3.65 (m, 1H), 4.00–4.02 (two s, O$\underline{\text{CH}}_3$), 7.01 (s, 1H), 7.5–8.5 (m, 4H).

EXAMPLE V

Preparation of 6,6α,7,8,9,10,10α,11-octahydro-5,12-dimethoxy-11-oxo-8-acetyl-naphthacene and 6,6α,7,8,9,10,10α,11-octahydro-5,12-dimethoxy-11-oxo-9-acetyl-naphthacene (7)

A solution of 0.45 g; 1.1 mmol of the mixture of isomeric compounds prepared in Example IV in 40 ml of ethanol and 0.2 ml of concentrated hydrochloric acid was hydrogenated at room temperature in the presence of 0.3 g of 5% palladium-on-charcoal as catalyst. The catalyst was filtered off and the solution was evaporated to a residue under reduced pressure. The residue was dissolved in 10 ml of concentrated sulphuric acid. After standing for 20 minutes the reaction mixture was poured into cold water, and then extracted with chloroform. The organic phase, washed with an aqueous saturated solution of sodium bicarbonate and then with water, was evaporated to a residue which was purified by chromatography on a column of silica gel, eluting with chloroform, to give 0.2 g of a mixture of the isomeric title compounds. TLC on kieselgel plates Merck $F_{254}$ (chloroform:acetone 98:2 by volume) Rf 0.33

EI-MS: m/e 352 (M+), m/e 337 (M—CH3), m/e 43 (CH3CO+).

IR spectrum (film): 1680 cm$^{-1}$ CO of acid, 1710 cm$^{-1}$ CO of ketone, 1730 cm$^{-1}$ CO of ester.

PMR (CDCl3): 1.5–2.6 δ (m, 8H), 2.18 (s, 3H, COCH3), 3.28 (m, 1H), 3.70 (s, 3H, OCH3), 8.53 (bs, 1H, COOH).

EXAMPLE IV

Preparation of 1,4-diemthoxy-3-(2'-methoxycarbonyl-4'-acetyl-cyclohexylcarbonyl)-naphthalene and 1,4-dimethoxy-3-(2'-methoxycarbonyl-5'-acetyl-cyclohexylcarbonyl)naphthalene [(6) R=CH3]

A solution of 3.2 g; 0.017 mol of 1,4-dimethoxynaphthalene and 4.0 g; 0.017 mol of the compound prepared in Example III in 50 ml of trifluoroacetic anhydride and 25 ml of trifluoroacetic acid was refluxed for 24 hours. The residue, obtained by evaporting off the solvents under reduced pressure, was dissolved in chloroform and washed with an aqueous saturated solution of sodium bicarbonate and then with water. The residue, obtained by evaporation of the solvent, was purified on a column of silica gel, using chloroform as the eluting solvent, to give 3.5 g of a mixture of the isomeric title compounds.

TLC kieselgel plates Merck $F_{254}$ (chloroform:acetone 98:2 by volume). Rf 0.3

FD-MS: m/e 398 (M+)

IR (film): 1660 cm$^{-1}$ CO of α,β-unsaturated ketone, 1710 cm$^{-1}$ CO of ketone, 1720 cm$^{-1}$ CO of ester.

PMR (CDCl3): 1.8–2.3 δ (m, 3H), 2.30 (s, 3H, COCH3), 2.6–3.1 (m, 4H), 7.4–8.4 (m, 5H), 11.71 and 11.75 (two s, 1H, OH phenolic).

UV-Vis (CHCl3): 250, 267; 414 nm

EXAMPLE VII

Preparation of 4-demethoxy-6,7-dideoxydaunomycinone (10) and 4-demethoxy-7,11-dideoxydaunomycinone (11)

A mixture (0.32 g) of compounds (8) and (9) prepared as described in Example VI, was dissolved in 38 ml of acetic anhydride and refluxed for 18 hours in the presence of 0.19 g of p-toluene-sulphonic acid. The residue, obtained by evaporation under reduced pressure of the reaction mixture, was dissolved in 40 ml of methylene dichloride and treated with 0.258 g of m-chloroperbenzoic acid. After 2 hours at room temperature the reaction mixture was washed with a saturated aqueous solution of sodium bicarbonate and then with water. The residue, obtained by evaporation of the solvent, was dissolved in a mixture of acetone and ethanol and treated with 30 ml of 1N sodium hydroxide for 1 hour at room temperature. After conventional processing, the crude product was chromatographed on a column of silica gel, using chloroform as the eluting agent, to afford the title compounds in pure form. Compound (10) TLC on kieselgel plates Merck $F_{254}$ (chloroform:acetone 98:2 by volume): Rf 0.18

EI-MS: m/e 336 (M+), 318 (M—H2O), 293 (M—CH3CO), 275 (M—CH3CO—H2O).

PMR 80 MHz (CDCl3): 1.95 δ (m, 2H, H-8), 2.38 (s, 3H, COCH3), 3.01 (m, 4H, H-7, H-10), 3.83 (s, 1H, OH-9), 7.64 (s, 1H, H-6), 7.70–8.3 (m, 4H, arom), 13.03 (s, 1H, OH-11).

IR (KBr): 1620 cm$^{-1}$ bonded C=O quinone, 1665 cm$^{-1}$ free C=O quinone, 1705 cm$^{-1}$ C=O ketone.

UV-Vis (CHCl3): 250, 267, 414 nm.

Compound (11) TLC on kieselgel plates Merck $F_{254}$ (chloroform:acetone 98:2 by volume): Rf 0.15.

EI-MS: m/e 336 (M+).

PMR-80 MHz (CDCl3): 2.0 δ (m, 2H, H-8), 2.38 (s, 3H, COCH3), 2.75–3.28 (two d, J=17.4 Hz, 2H, H-10), 3.0 (m, 2H, H-7), 3.75 (s, 1H, OH-9), 7.51 (s, 1H, H-11), 7.7–8.4 (m, 4H, arom), 12.99 (s, 1H, OH-6).

UV-Vis (CHCl3): 250, 267, 414 nm.

IR (KBr): 1625 cm$^{-1}$ bonded C=O quinone, 1665 cm$^{-1}$ free C=O quinone, 1705 cm$^{-1}$ C=O ketone.

EXAMPLE VIII

Preparation of (±)4-demethoxy-6-deoxydaunomycinone (II: $R_1$=OH, $R_2$=H)

A solution of 0.5 g of (±)4-demethoxy-6,7-dideoxydaunomycinone (10), prepared as described in Example VII, in 50 ml of benzene was treated at reflux temperature for 4 hours with 1.2 ml of ethylene glycol in the presence of 0.045 g of p-toluenesulphonic acid, to form the corresponding 13-ketal derivative (0.4 g) which crystallized directly from the cooled reaction mixture. This ketal compound was dissolved in 250 ml of carbon tetrachloride and treated with 2 ml of a solution of 3.2 g of bromine in 32 ml of carbon tetrachloride at 45° C. for 6 hours in the presence of 0.46 g of 2,2'-azobis-isobutyronitrile. The cooled reaction mixture was extracted with 1N aqueous sodium hydroxide and the colored aqueous phase was adjusted to pH 8.5 and extracted with chloroform. The chloroform extracts, after being evaporated to a small volume, afforded 0.11 g of crystalline 4-demethoxy-6-deoxy-13-ketal daunomycinone.

TLC on kieselgel plates (Merck $F_{254}$) solvent system CHCl3—(CH3)2CO (9:1 v/v): Rf 0.21.

EI-MS: m/e 396 (M+).

PMR (CDCl3): 1.47 δ (s, 3H, 14-CH3), 1.53 (s, 1H, OH-9), 2.27 (ddd, 2H, H-8) J=14.5 Hz, 4.5 Hz, 6.0 Hz, 3.02 (dd, 2H, H-10) J=17.5 Hz, 3.90 (d, 1H, OH-7) J=10.5 Hz, 4.09 (s, 4H, OCH2CH2O), 4.90 (dd, 1H, H-7) J=4.5, 6.0 Hz, 7.85, 8.26 (m, 4H, aromatic), 7.98 (s, 1H, H-6), 13.11 (S, 1H, OH-11).

IR (KBr): 1620 cm$^{-1}$ bonded C=O quinone, 1670 cm$^{-1}$ free C=O quinone.

Finally the hydrolysis of the ketal group was performed by treatment with an aqueous solution of hydrogen chloride in acetone (300 ml of a 0.25N solution) at room temperature for 3 hours).

Compound II ($R_1$=OH, $R_2$=H): TLC on kieselgel plates (Merck $F_{254}$) using solvent system chloroform:acetone (9:1 by volume): Rf 0.24

FD-MS: m/z 352 (M+).

PMR 270 MHz (CDCl3): 2.42 (s, 3H, COCH3), 2.98 (d, 1H, $H_{ax}$-10, $J_{gem}$17.9 Hz), 3.13 (d, 1H, $H_e$-10, $J_{gem}$ 17.9 Hz), 4.07 (d, OH-7, J=10 Hz), 4.46 (s, OH-9), 4.93 (m, $H_{eq}$-7, J=10 Hz after D2O addition $W_H$=8 Hz), 7.99 (s, H-6), 13.07 (s, OH-11).

EXAMPLE IX

Preparation of
(±)4-demethoxy-11-deoxydaunomycinone (II: $R_1=H$, $R_2=OH$)

Compound (11), prepared as described in Example VII, is converted to the title compound following the procedure described in Example VIII. Compound II ($R_1=H$, $R_2=OH$): TLC on silica gel plates (Merck $F_{254}$) solvent system chloroform:acetone (9:1 by volume): Rf 0.34

PMR 60 Mz (CDCl$_3$/DMSO-d$_6$): 2.42 (s, CH$_3$CO), 3.08 (d, H$_{ax}$-10, J$_{gem}$ 18 Hz), 3.28 (d, H$_{eq}$-10, J$_{gem}$ 18 Hz), 5.32 (m, H$_{eq}$-7 W$_H$=10 Hz), 6.62 (s, H-11), 13.24 (s, OH-6), 7.7–8.5 (m, 4 aromatic protons).

EXAMPLE X

Preparation of 4-demethoxy-6-deoxydaunorubicin and 7,9-diepi-4-demethoxy-6-deoxydaunorubicin To a solution of 0.065 g of racemic 4-demethoxy-6-deoxydaunomycinone (II: $R_1=OH$, $R_2=H$), prepared as described in Example VIII, in 45 ml of anhydrous dichloromethane, there were added 1 g of molecular sieve (4 Å Merck), 0.079 g of 2,3,6-trideoxy-3-trifluoroacetamido-4-O-trifluoroacetyl-α-L-lyxopyranosyl chloride (III: Y=Cl, $R_6$=CF$_3$COO, $R_7$=H), 0.029 ml of sym-collidine and 0.057 g of silver trifluoromelthanesulphonate dissolved in 2 ml of anhydrous diethyl ether. After 2 hours at room temperature the reaction mixture was filtered and washed with aqueous 0.1N hydrochloric acid, water, aqueous saturated sodium bicarbonate solution, and water. Then the residue obtained by the evaporation of the solvent was taken up in methanol and after 30 minutes at room temperature the hydrolysis of the C-4'-O-trifluoroacetyl group was completed. This afforded a mixture of the diastereoisomers N-trifluoroacetyl-4-demethoxy-6-deoxydaunorubicin and 7,9-diepi-N-trifluoroacetyl-4-demethoxy-6-deoxydaunorubicin: TLC on kieselgel plates (Merck $F_{254}$) using the solvent system chloroform:acetone (4:1 by volume): Rf 0.16 and 0.13.

The pure diastereoisomers are obtained by chromatographic separation on a column of silica gel using, as eluent, the solvent system chloroform:acetone (6:1 by volume).

The hydrolysis of the N-protecting group was performed by dissolving the N-trifluoroacetyl derivative in aqueous 0.1N sodium hyroxide. After 30 minutes at 0° C. the solution was adjusted to pH 8 and extracted with chloroform. Evaporation of the solvent to a small volume, followed by addition of methanolic 0.1N hydrogen chloride in order to adjust the pH to from 4.5 to 5, afforded 4-demethoxy-6-deoxydaunorubicin and 7,9-diepi-4-demethoxy-6-deoxydaunorubicin, as the hydrochlorides.

TLC on silica gel plates (Merck $F_{254}$) using the solvent system chloroform:methanol:acetic acid:water (80:20:7:3 by volume) Rf 0.26 and 0.30.

FD-MS: m/z 482 (MH+); 481 (M+).

EXAMPLE XI

Preparation of
4-demethoxy-4'-epi-6-deoxydaunorubicin and
4-demethoxy-4'-epi-7,9-diepi-6-deoxydaunorubicin The coupling reaction between racemic 4-demethoxy-6-deoxydaunomycinone (II: $R_1=OH$, $R_2=H$) and 2,3,6-trideoxy-3-trifluoroacetamido-4-O-trifluoroacetyl-α-L-arabino-pyranosyl chloride (III: Y=Cl, $R_6$=H, $R_7$=CF$_3$COO) operating in accordance with the procedure described in Example X afforded 4-demethoxy-4'-epi-6-deoxy-N-trifluoroacetyldaunorubicin and the corresponding 7,9-diepi derivative. Mild Alkaline treatment effected hydrolysis of the N-trifluoroacetyl group giving 4-demethoxy-4'-epi-6-deoxydaunorubicin and 4-demethoxy-4'-epi-7,9-diepi-6-deoxydaunorubicin, isolated as the hydrochlorides.

EXAMPLE XII

Preparation of 4-demethoxy-4',6-dideoxydaunorubicin and 4-demethoxy-4',6'-dideoxy-7,9-diepidaunorubicin The coupling reaction between racemic 4-demethoxy-6-deoxydaunomycinone (II: $R_1=OH$, $R_2=H$) and 2,3,4,6-tetradeoxy-3-trifluoroacetamido-L-threopyranosyl chloride (III: Y=Cl, $R_6=R_7=H$) operating in accordance with the procedure described in Example X afforded 4-demethoxy-4',6'-dideoxy-N-trifluoroacetyldaunorubicin and the corresponding 7,9-diepi derivative. Mild alkaline treatment effected hydrolysis of the N-trifluoroacetyl group giving 4-demethoxy-4',6-dideoxydaunorubicin and 4-demethoxy-4',6-dideoxy-7,9-diepidaunorubicin isolated as the hydrochlorides.

EXAMPLE XIII

Preparation of 4-demethoxy-6-deoxy-doxorubicin

Following the process described in U.S. Pat. No. 3,803,124 and using as the starting material 4-demethoxy-6-deoxydaunorubicin prepared according to Example X, the title compound was isolated as the hydrochloride.

EXAMPLE XIV

Preparation of 4-demethoxy-4'-epi-6-deoxydoxorubicin

Following the process described in U.S. Pat. No. 3,803,124 and using as the starting material 4-demethoxy-4'-epi-6-deoxydaunorubicin prepared according to Example XI, the title compound was isolated as the hydrochloride.

EXAMPLE XV

Preparation of 4-demethoxy-4',6-dideoxydoxorubicin

Following the process described in U.S. Pat. No. 3,803,124 and using as the starting material 4-demethoxy-4',6-dideoxydaunorubicin prepared according to Example XII, the title compound was isolated as the hydrochloride.

EXAMPLE XVI

Preparation of
4-demethoxy-4'-epi-11-deoxydaunorubicin and
4-demethoxy-4',7,9-triepi-11-deoxydaunorubicin To a solution of 0.7 g of racemic 4-demethoxy-11-deoxydaunomycinone (II: $R_1=H$, $R_2=OH$), prepared as described in Example IX, in 100 ml of anhydrous dichloromethane were added 6 g of molecular sieve (4 Å Merck), 0.785 g of 2,3,6-trideoxy-3-trifluoroacetamido-4-O-trifluoroacetyl-α-L-arabinopyranosyl chloride (III: Y=Cl, $R_6$=H, $R_7$=CF$_3$COO), 0.26 ml of sym-collidine and 0.515 g of silver trifluoromethanesulphonate dissolved in 25 ml of anhydrous diethyl ether. After 20 minutes at room temperature the reaction mixture was filtered and washed with aqueous 0.1N hydrochloric acid, water, aqueous saturated sodium bicarbonate solution and water. Then the residue obtained by evaporating off the solvent was taken up in methanol overnight. Evaporation of the methanol afforded a mixture of the diastereoisomers N-trifluoroacetyl-4-demethoxy-4'-epi-11-deoxydaunorubicin and N-trifluoroacetyl-4-demethoxy-4',7,9-triepidaunorubicin. TLC on kieselgel plates (Merck $F_{254}$) using the solvent system chloroform:methanol (4:1 by volume): Rf 0.13 and 0.16, respectively. The pure diastereoisomers were obtained by chromatographic separation on a column of silica gel using, as eluent, the solvent system chloroform:acetone (97:3 by volume). N-trifluoroacetyl-4-demethoxy-4'-epi-11-deoxydaunorubicin (0.34 g), m.p. 208°–210° C., and N-trifluoroacetyl-4-demethoxy-4',7,9-triepi-11-deoxydaunorubicin, m.p. 198°–200° C.

3 g of N-trifluoroacetyl-4-demethoxy-4'-epi-11-deoxydaunorubicin were dissolved in 25 ml of acetone and 25 ml of aqueous 0.2N sodium hydroxide. After 30 minutes at room temperature the reaction mixture was adjusted to pH 3.5 with hydrochloric acid and extracted with chloroform to eliminate impurities. Then the aqueous solution was adjusted to pH 8 and extracted with chloroform. The evaporation of the solvent to a small volume followed by addition of methanolic hydrogen chloride and precipitation with diethyl ether afforded 4-demethoxy-4'-epi-11-deoxydaunorubicin, as the hydrochloride (0.23 g), m.p. 175°–176° C. TLC on kieselgel plates (Merck $F_{254}$) using the solvent system chloroform:methanol:acetic acid 40:10:1 by volume): Rf 0.22.

FD-MS: m/z 482 (MH+); 481 (M+).

PMR 60 MHz ($D_2O$): 1.35 (d, $CH_3$-5') 2.42 (s, $CH_3CO$-9), 2.90 (s, $CH_2$-10), 3.2–3.6 (m, H-3', H-4'), 4.05 (m, H-5'), 5.25 (s Broad, H-1' $W_H$=6 Hz), 6.96 (s, H-11), 7.76 (s, broad, 4 aromatic protons).

The hydrolysis of the N-trifluoroacetyl group of the other diastereoisomer operating analogously afforded 4-demethoxy-4',7,9-triepi-11-deoxydaunorubicin. TLC on kieselgel plates (Merck $F_{254}$) using the same solvent system Rf 0.24.

EXAMPLE XVII

Preparation of 4-demethoxy-11-deoxydaunorubicin and 4-demethoxy-7,9-diepi-11-deoxydaunorubicin The coupling reaction between 0.100 g of racemic 4-demethoxy-11-deoxydaunomycinone (II: $R_1$=H, $R_2$=OH) and 0.11 g of 2,3,6-trideoxy-3-trifluoroacetamido-4-O-trifluoroacetyl-α-L-lyxopyranosyl chloride (III: Y-Cl, $R_6$=$CF_3COO$, $R_7$=H) operating in accordance with the procedure described in Example XVI afforded 4-demethoxy-11-deoxy-N-triflyoroacetyldaunorubicin, Rf 0.24, and the corresponding 7,9-diepi derivative. Mild alkaline tretment afforded the hydrolysis of the N-trifluoroacetyl group giving 4-demethoxy-11-deoxydaunorubicin, as its hydrochloride, m.p. 104°–105° C., TLC Rf 0.17 (chloroform:methanol:acetic acid 40:10:1 by volume), FD-MS: m/z 482 (MH+), 481 (M+), and 4-dememthoxy-7,9-diepi-11-deoxydaunorubicin, as the hydrochloride.

EXAMPLE XVIII

Preparation of 4-demethoxy-4',11-dideoxydaunorubicin and 4-demethoxy-4',11-dideoxy-7,9-diepi-daunorubicin The coupling reaction between 0,35 g of racemic 4-demethoxy-11-deoxydaunomycinone (11: $R_1$=H, $R_2$=OH) prepared as described in example IX, in 50 ml of anhydrous dichloromethane and 0.245 of 2,3,4,6-tetradeoxy-3-trifluoroacetamido-L-threopyranosyl chloride (III:Y=Cl, $R_6$=$R_7$=H) operating in accordance with the procedure described in example XVI afforded after chromatographic separation on column of silica gel using as eluent the solvent system toluene-acetone (96:4 v/v), 4-demethoxy-4',11-dideoxy-N-trifluoroacetyldaunorubicin [g 0.170, TLC on kieselgel plates (Merck $F_{254}$) using solvent system toluene-acetone (4:1 v/v): Rf 0.53] and 4-demethoxy-4',11-dideoxy-7,9-diepi-N-trifluoroacetyl-daunorubicin [g 0.2, TLC on kieselgel plates (Merck $F_{254}$) using solvent system toluene-acetone (4:1 v/v): Rf 0.53] Mild alkaline treatment afforded the hydrolysis of the N-trifluoroacetyl group giving 4-demethoxy-4',11-deoxydaunorubicin, isolated as its hydrochloride, m.p. 155°–156°, TLC: Rf 0.40 (chloroform-methanol-acetic acid-water 80:20:7:3 by volume).

FD-MS: m/z 466 (MH+); 465 (M+)

EXAMPLE XIX

Preparation of 4-demethoxy-11-deoxy-4'-epidoxorubicin

Following the process described in U.S. Pat. No. 3,803,124 and using as the starting material 4-demethoxy-11-deoxy-4'-epidaunorubicin, prepared according to Example XVI, the title compound was isolated as the hydrochloride.

EXAMPLE XX

Preparation of 4-demethoxy-11-deoxy-doxorubicin

Following the process described in U.S. Pat. No. 3,803,124 and using as the starting material 4-demethoxy-11-deoxy-daunorubicin, prepared according to Example XVII, the title compound was isolated as the hydrochloride.

EXAMPLE XXI

Preparation of 4-demethoxy-4',11-dideoxydoxorubicin

Following the process described in U.S. Pat. No. 3,803,124 and using as the starting material 4-demethoxy-4'-11-dideoxy-daunorubicin, prepared according to Example XVIII, the title compound was isolated as the hydrochloride.

BIOLOGICAL ACTIVITY

The biological activity of the following compound was tested against Hela cells in vitro:
4-demethoxy-4'-epi-11-deoxydaunorubicin
4-demethoxy-11-deoxy-4'-epidoxorubicin
4-demethoxy-11-deoxydaunorubicin
4-demethoxy-6-deoxydaunorubicin The data in Table 1 show that all of these compounds exert remarkable cytotoxic activity in vitro.

The activity of the compounds 4-demethoxy-4'-epi-11-deoxydaunorubicin and was also tested against P388 ascitic leukemia in mice. The data in Table 2 show that both of these compounds exert antitumor activity.

TABLE 1

| Compound | Effect on Hela cells cloning activity[a] | | $ID_{50}$ (ng/ml) |
|---|---|---|---|
| | Dose (ng/ml) | % | |
| Daunorubicin | 25 | 21, 42, 50, 8, 16, | 15 |
| | 12.5 | 65, 83, 80, 77, 79 | |
| | 6.2 | 86, 150, 104, 93, 101, | |
| | 3.1 | 104, 115 | |
| 4-demethoxy-4'-epi- | 100 | 13, 10 | 40 |

TABLE 1-continued

| | Effect on Hela cells cloning activity[a] | | |
|---|---|---|---|
| Compound | Dose (ng/ml) | % | ID$_{50}$ (ng/ml) |
| 11-deoxy-daunorubi-cin | 25 | 56, 82 | |
| | 6.2 | 60, 105 | |
| | 1.5 | 78, 109 | |
| 4-demethoxy-11-deoxydaunorubicin | 100 | 0 | 25 |
| | 25 | 50 | |
| | 6.2 | 112 | |
| 4-demethoxy-11-deoxy-4'-epidoxorubicin | 400 | 0 | 20 |
| | 100 | 1 | |
| | 25 | 33 | |
| | 6.2 | 100 | |
| 4-demethoxy-6-deoxydaunorubicin | 250 | 0 | 17 |
| | 50 | 4 | |
| | 10 | 73 | |
| | 5 | 119 | |

[a]Treatment for 24 hours

TABLE 2

| | Effect against P388 leukemia[a] | | | |
|---|---|---|---|---|
| Compound | Dose[b] (ng/kg) | T/C[c] % | LTS[d] | Toxic[e] deaths |
| Daunorubicin | 2.9 | 180 | 0/10 | 0/10 |
| | 4.4 | 185 | 0/10 | 0/10 |
| | 6.6 | 190 | 0/10 | 3/10 |
| 4-demethoxy-4'-epi-11-deoxy-daunorubicin | 6.6 | 160 | 0/10 | 0/10 |
| | 10 | 160 | 0/10 | 0/10 |
| | 15 | 160 | 0/10 | 0/10 |
| 4-demethoxy-deoxy-daunorubi-cin | 4.4 | 155 | 0/10 | 0/10 |
| | 6.6 | 120 | 0/10 | 7/10 |
| | 10 | 90 | 0/10 | 8/10 |

[a]BDFl mice were injected ip with 10$^6$ leukemia cells.
[b]Treatment ip on day 1 after tumor inoculum.
[c]Median survival time of treated mice/median survival time of controls × 100.
[d]Long term survivors.
[e]Toxic deaths, evaluated on the basis of zooptic findings.

What we claim is:

1. An anthracycline glycoside of the formula:

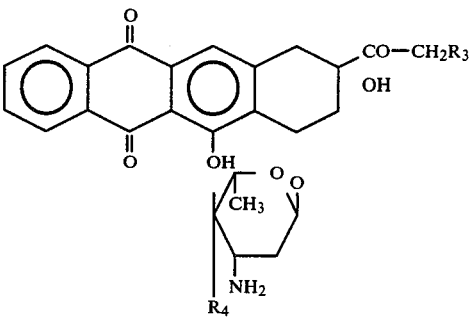

wherein each of $R_3$ and $R_4$ is independently selected from the group consisting of hydrogen and hydroxy, and the pharmaceutically acceptable acid addition salts thereof.

2. A compound according to claim 1 which is 4-demethoxy-4'-epi-11-deoxydaunorubicin.

3. A compound according to claim 1 which is 4-demethoxy-4',11-dideoxydaunorubicin.

4. A compound according to claim 1 which is 4-demethoxy-11-deoxy-4'-epidoxorubicin.

5. A compound according to claim 1 which is 4-demethoxy-4',11-dideoxydoxorubicin.

6. A pharmaceutical composition for inhibiting the growth of P388 leukemia comprising a therapeutically effective amount of a compound according to claim 1 in combination with an inert carrier therefor.

7. A method of inhibiting the growth of P388 leukemia, said method comprising administering to a mammal afflicted therewith, a therapeutically effective amount of a compound according to claim 1.

* * * * *